US00PP32935P2

(12) United States Plant Patent

Van Swieten

(10) Patent No.: US PP32,935 P2
(45) Date of Patent: Mar. 30, 2021

(54) *PHALAENOPSIS* ORCHID PLANT NAMED 'PHALIJBAK'

(50) Latin Name: ***Phalaenopsis* hybrid**
Varietal Denomination: PHALIJBAK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/910,338

(22) Filed: Jun. 24, 2020

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./311
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALIJBAK', particularly characterized by small, very light purple, striped flowers with purplish-pink and very light purple lips, few branches, flat flower shape, and is propagated by meristem tissue culture, is disclosed.

3 Drawing Sheets

Genus and species: *Phalaenopsis* hybrid.
Variety denomination: 'PHALIJBAK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIJBAK'.

The new *Phalaenopsis* plant is a product of a planned breeding program conducted by the inventor in Bleiswijk, the Netherlands. The objective of this breeding program was to create a new *Phalaenopsis* plant with few branches and very light purple, striped flowers with purplish-pink and very light purple lips, suitable for potted plant production.

The new *Phalaenopsis* plant 'PHALIJBAK' is a result of cross-pollination made by the inventor in February 2012 in Bleiswijk, the Netherlands, of the proprietary female, or seed parent, *Phalaenopsis* hybrid '01-3358' (unpatented) with the proprietary male, or pollen parent, *Phalaenopsis* hybrid '11968-04' (unpatented).

The new *Phalaenopsis* was selected by the inventor as a single plant within the progeny of the stated cross-pollination in a controlled greenhouse in Bleiswijk, the Netherlands, in January 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 20, 2019 (Application no. 2019/2327), by Applicant who obtained the subject matter disclosed directly from the inventor. 'PHALIJBAK' has not been made publicly available or sold anywhere in the world prior to the effective filing date of this application with the exception of sales or disclosures made one year or less before the effective filing date of this claimed invention by Applicant who obtained 'PHALIJBAK' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIJBAK' as a new and distinct variety of *Phalaenopsis* plant:

1) Small, very light purple, striped flowers with purplish-pink and very light purple lips;
2) Plant has few branches; and
3) Flower shape is flat.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in May 2020. Colors in the photographs may differ from the color values cited in the detailed botanical description, which accurately describe the actual colors of the new variety.

DESCRIPTION OF THE NEW VARIETY

Figure 1:
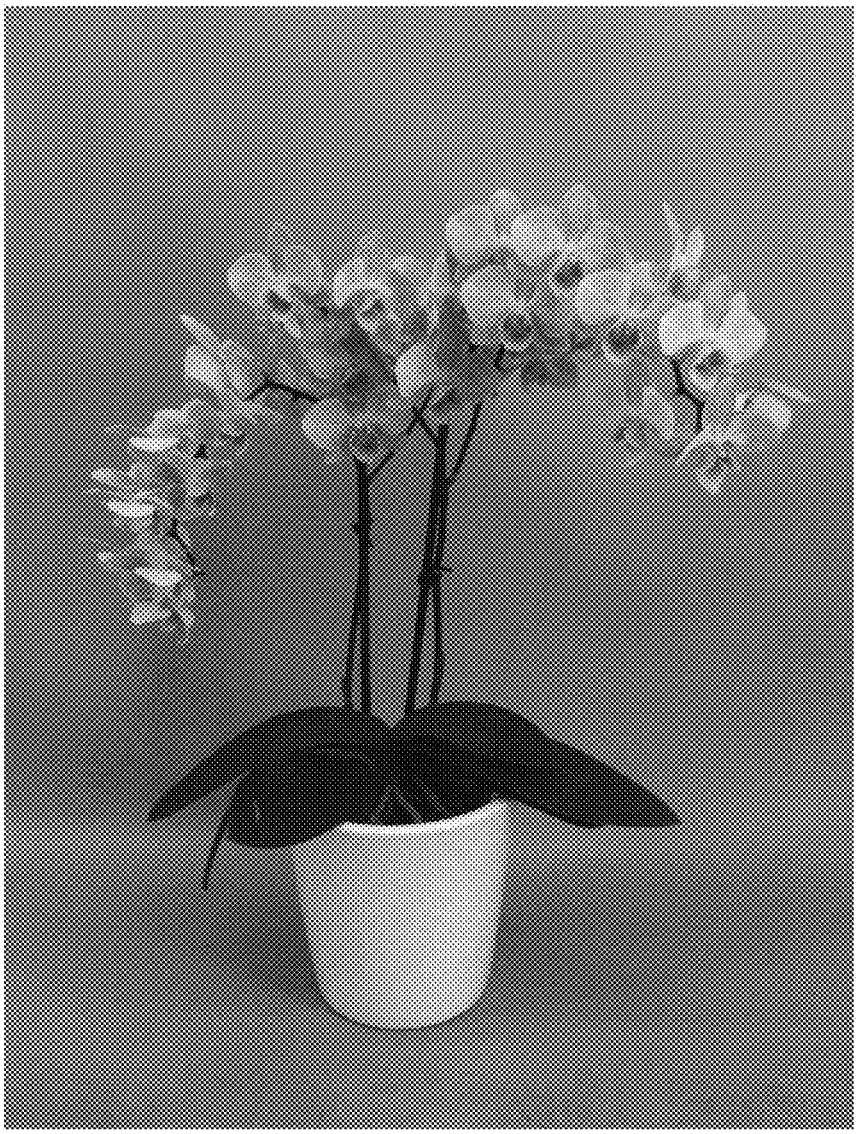
FIG. 1 shows the overall plant habit, including blooms and foliage of 'PHALIJBAK'.
Figure 2:
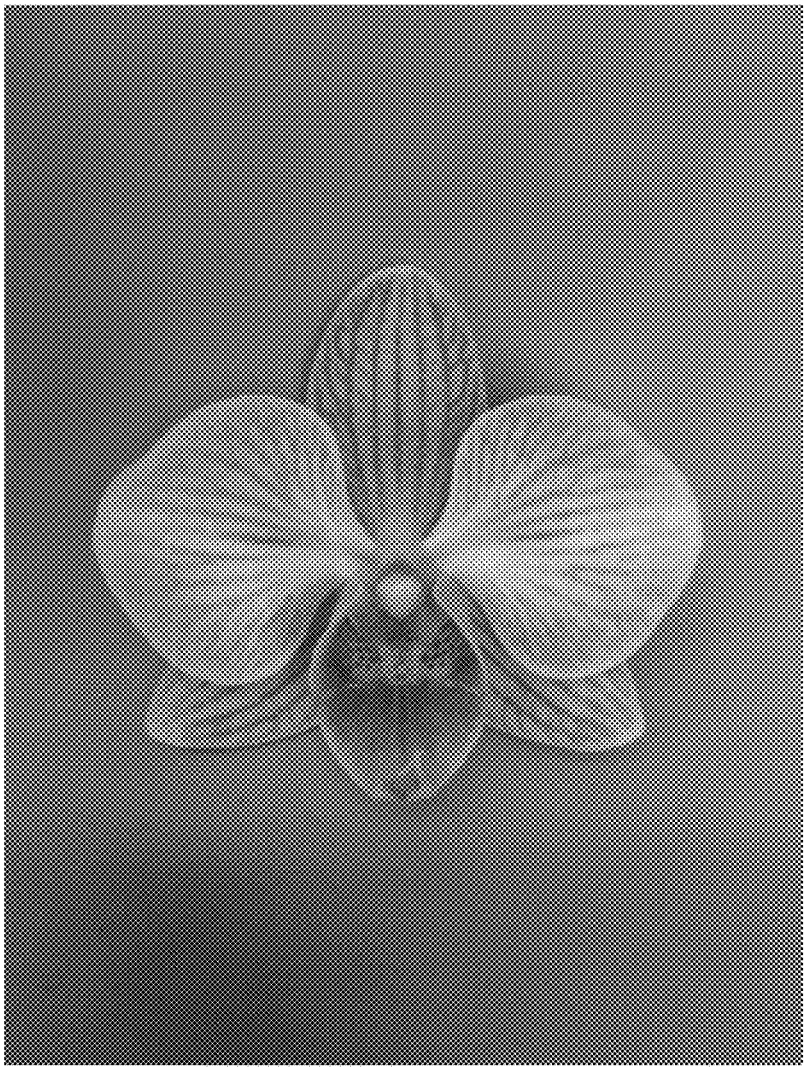
FIG. 2 shows a close-up of a flower of 'PHALIJBAK'.
Figure 3:
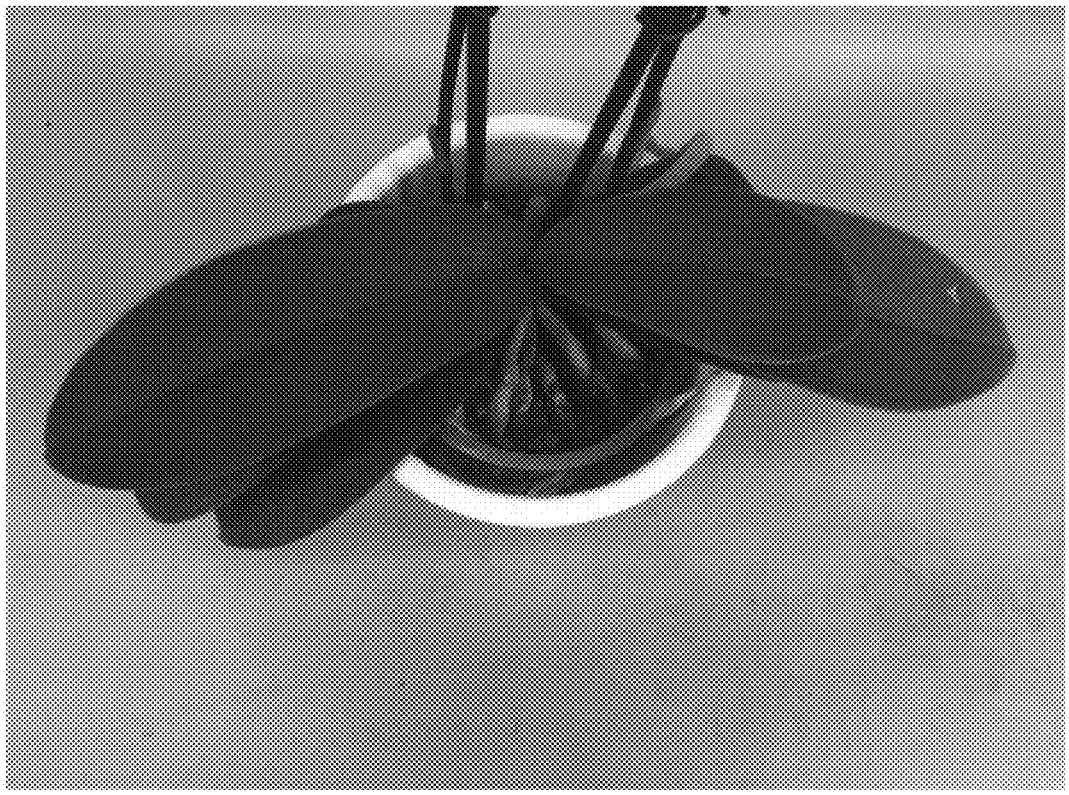
FIG. 3 shows an overhead view of the leaves of 'PHALIJBAK'.

The following detailed description sets forth the distinctive characteristics of 'PHALIJBAK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALIJBAK'.

Parentage:

*Female parent*.—*Phalaenopsis* cultivar '01-3358' (unpatented).

*Male parent*.—*Phalaenopsis* cultivar '11968-04' (unpatented).

Propagation:

*Type*.—Meristem tissue culture.

Roots:

*Root description*.—Greyed-green (something between RHS 190B and 190C) colored roots with branching lateral roots having yellowish-green (RHS N144A) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 40.0 cm to 45.0 cm.

*Width* (*measured from leaf tips*).—About 30.0 cm to 33.0 cm.

*Vigor*.—Strong.

Leaves:

*Mature leaves*.—Quantity per plant: 8 to 10 leaves are produced before flowering. Length (fully expanded): 15.0 cm to 17.0 cm. Width: 6.0 cm to 7.0 cm. Position of the broadest part of the leaf: Toward the apex. Shape: Obovate. Base shape: Moderately elongated. Apex: Unequal obtuse. Leaf blade angle with the petiole (measured from the horizontal position): Between 10 degrees and 25 degrees. Leaf margin: Entire. Color: Upper surface: RHS 146A. Lower surface: RHS 146B. Texture (both upper and lower surfaces): Smooth. Thickness: 2.0 mm to 2.3 mm. Variegation: Absent. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—16 to 26.

*Length*.—40.0 cm to 45.0 cm.

*Diameter*.—3.6 mm to 4.6 mm.

*Strength*.—Moderately strong.

*Aspect*.—Upright to slightly pendent.

*Texture*.—Smooth.

*Color*.—Brown (something in between RHS 200A and 200B).

*Internode length*.—2.0 cm to 3.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 3.

*Inflorescence size*.—Height (from base to tip): 220.0 mm to 270.0 mm.

*Flowering time*.—First flowers can be expected 10 to 11 months after planting in a 12-cm pot.

*Flower*.—Height: 48.0 mm to 53.0 mm. Diameter: 57.0 mm to 62.0 mm. Depth of lip: 17.0 mm to 19.0 mm.

*Flower longevity*.—On the plant: 11 to 13 weeks.

*Flower shape*.—Flat.

*Fragrance*.—Absent.

*Flower bud*.—Average size: Medium. Length: 17.0 mm to 19.0 mm. Width: 13.0 mm to 15.0 mm. Shape: Egg shaped. Color: Light yellow-green (RHS 145C) at the base and purplish-red (RHS N77B) toward the tip.

*Petals*.—Arrangement: Open/free. Shape: Semi-circular. Apex: Rounded asymmetric. Margin: Entire. Length (from base to tip): 28.0 mm to 30.0 mm. Width: 25.0 mm to 27.0 mm. Position of the broadest part of the petal: Toward the base. Color (when fully opened): Upper surface: Basic color: Very light purple (RHS 76B). Over color: White (RHS NN155C) at the base and toward the apex. Lower surface: Basic color: Very light purple (RHS 76C). Over color: Stripes (RHS 76A). Number of spots and stripes on the petals (upper surface): Medium to many stripes. Color of spots and stripes on the petals (upper surface): RHS N78D. Density of netting of the petals (upper surface): None. Color of the netting (upper surface): None.

*Dorsal sepal*.—Shape: Elliptic. Apex: Obtuse symmetric. Margin: Entire. Length (from base to tip): 27.0 mm to 29.0 mm. Width: 17.0 mm to 19.0 mm. Position of the broadest part of the dorsal sepals: At the middle. Color (when fully opened): Upper surface: Basic color: Light reddish-purple (RHS N78C). Over color: Reddish-purple stripes (RHS N78B). Lower surface: Basic color: Very light purple (something in between RHS 76B and 76C). Over color: Light reddish-purple stripes (RHS N78D). Number of spots and stripes on the dorsal sepals (upper surface): Many stripes. Color of spots and stripes on the dorsal sepals (upper surface): RHS N78B. Density of netting of the dorsal sepals (upper surface): None. Color of the netting: None.

*Lateral sepals*.—Shape: Ovate. Apex: Acute symmetric. Margin: Entire. Length (from base to tip): 27.0 mm to 29.0 mm. Width: 15.0 mm to 17.0 mm. Position of the broadest part of the lateral sepals:

Toward the base. Color (when fully opened): Upper surface: Basic color: Very light purple (RHS 76C). Over color: Purplish-pink stripes (RHS N78C). Lower surface: Basic color: Very light purple (RHS 76B). Over color: Purplish-pink (RHS N78C) at the base; light reddish-purple stripes (RHS N78D). Number of spots and stripes on the lateral sepals (upper surface): Many stripes. Color of spots and stripes on the lateral sepals (upper surface): RHS N78C. Density of netting of the lateral sepals (upper surface): None. Color of the netting (upper surface): None.

*Labellum* (*lip*).—Whiskers: Present. Length of whiskers: 4.0 mm to 6.0 mm. Color of whiskers: Purplish-pink (RHS N78C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 14.0 mm to 16.0 mm. Width: 8.0 mm to 10.0 mm. Color: Upper surface: White (RHS NN155C) at the base; light greenish-yellow (RHS 4C) at margin on one side; reddish-purple (RHS N78A) and mix of purplish-pink (RHS N78C) and light purple (RHS 76A) toward the other margin. Lower surface: Hint of white (RHS N155C) at the base; light yellow-green (RHS 4D) at the margin on one side; mix of light purple (RHS 76A) and purplish-pink (RHS N78C) toward margin on the other side. Number of spots, dots, and stripes on the lateral lobe: Few stripes and dots at base. Color of spots, dots, and stripes on the lateral lobe: Purplish-red (RHS 71A). Density of netting of the lateral lobe: None. Color of the netting: None.

*Apical lobe*.—Shape: Triangular to ovate. Margin: Entire. Length: 15.0 mm to 17.0 mm. Width: 13.0 mm to 15.0 mm. Color: Upper surface: Light greenish-yellow (RHS 4C) toward the wings on both sides; purplish-pink (RHS N78C) and very light purple (RHS 76C) toward whiskers. Lower surface: Light yellow (something in between RHS 4C and 4D) toward the wings on both sides; hint of purplish-pink (RHS N78C) at the base and very light purple (RHS 76C) toward whiskers. Number of spots and stripes on the apical lobe: Few stripes at the base. Color of spots and stripes on the apical lobe: RHS 71A. Density of netting of the apical lobe: None. Color of the netting: None.

*Callus*.—Average size: Small. Height: 0.4 cm to 0.5 cm. Length: 0.4 cm to 0.5 cm. Width: 0.3 cm to 0.4 cm. Color: Light greenish-yellow front and tips (RHS 8A); white (RHS NN155C) with very small spots (RHS 184C).

Reproductive organs:

*Column*.—Length: 8.0 mm to 10.0 mm. Diameter: 3.0 mm to 4.0 mm. Color: White (RHS NN155C) at the base; purplish-pink (RHS 76A) toward the tip.

*Pollinia*.—Quantity: 2. Diameter: 0.7 mm to 0.9 mm. Color: Orange-yellow (RHS 23A).

*Ovary*.—Length: 9.0 mm to 11.0 mm. Diameter: 1.5 mm to 1.7 mm.

*Pedicel*.—Length: 31.0 mm to 33.0 mm. Diameter: 1.8 mm to 2.1 mm. Texture: Smooth. Color: Yellow-green (RHS 144B) at the base; light yellow-green (RHS 145C) with a hint of very light purple (something in between RHS 76A and 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIJBAK' differs from female parent plant '01-3358' (unpatented) in that 'PHALIJBAK' has striped flowers with a basic color of very light purple, whereas '01-3358' has striped and shaded flowers with a basic color of purplish-pink.

'PHALIJBAK' differs from male parent plant '11968-04' (unpatented) in that 'PHALIJBAK' has flowers with a basic color of very light purple and brown peduncles, whereas '11968-04' has flowers with a basic color of white and green peduncles. Additionally, 'PHALIJBAK' has wider petals than '11968-04'.

'PHALIJBAK' is most similar to the commercial *Phalaenopsis* plants named 'PHALDONFI' (U.S. Plant Pat. No. 26,066) and 'PHALFAUF' (U.S. Plant Pat. No. 30,992). 'PHALIJBAK' differs from the commercial variety 'PHALDONFI' in that 'PHALIJBAK' has weakly spatulate lateral lobes, whereas 'PHALDONFI' has spatulate lateral lobes. Additionally, 'PHALIJBAK' has shorter leaves and larger flowers than 'PHALDONFI'.

'PHALIJBAK' differs from the commercial variety 'PHALFAUF' in that 'PHALIJBAK' has longer leaves, larger flowers, and longer whiskers than 'PHALFAUF'.

I claim:

1. A new and distinct variety of *Phalaenopsis* plant named 'PHALIJBAK', substantially as described and illustrated herein.

* * * * *